United States Patent [19]

Chen

[11] Patent Number: 6,046,391
[45] Date of Patent: Apr. 4, 2000

[54] PARENTAL COMBINATION METHOD FOR BREEDING PURPLE DOTTED PEONY

[76] Inventor: Dezhong Chen, Heping Peony Garden, Yuzhong County, 730101 Lanzhou, China

[21] Appl. No.: 09/066,342

[22] PCT Filed: Apr. 26, 1996

[86] PCT No.: PCT/CN96/00028

§ 371 Date: Apr. 27, 1998

§ 102(e) Date: Apr. 27, 1998

[87] PCT Pub. No.: WO97/16063

PCT Pub. Date: May 9, 1997

[30] Foreign Application Priority Data

Oct. 27, 1995 [CN] China ................................. 95117095

[51] Int. Cl.[7] ........................................................ A01H 5/00
[52] U.S. Cl. ........................... 800/323; 800/298; 800/260; Plt./316
[58] Field of Search ............................. Plt./316; 800/260, 800/298, 323

[56] References Cited

PUBLICATIONS

Sakata et al. Petal coloration and pigmentation of tree peony bred and selected in Daikon Island (Shimane Prefecture). Journal of the Japanese Society for Horticultural Science, vol. 64, pp. 351–357, 1995.

Zhang Yuexian. The breeding of Heze peony's new varieties by selection. Acta Horticultural, No. 404, pp. 171–174, 1995.

*Primary Examiner*—Lynette R. F. Smith
*Assistant Examiner*—Melissa L. Kimball
*Attorney, Agent, or Firm*—Pennie & Edmonds LLP

[57] ABSTRACT

The invention relates to a method for breeding purple dotted peony. 530 excellent peony varieties were obtained through parent selection, hybridization and screening. The flowers of these varieties have bright colors and pleasant fragrance. These varieties exhibit strong hardiness.

3 Claims, No Drawings

PARENTAL COMBINATION METHOD FOR BREEDING PURPLE DOTTED PEONY

TECHNICAL FIELD

The present invention relates to a method of flower breeding techniques, particularly the present invention relates to the parental combination method for breeding purple dotted peony.

PRIOR ART

The peony (*Paeonia suffruticosa*) is a deciduous bush. It has feather-like compound leaves with stalks, and its folioles are egg-shaped or elliptic. Its flowers are usually big with deep red, pink or white colors. Peony is a famous decorative plant, whereas medical preparations made from its bark can be used as antipyretic, and can invigorate the circulation of blood and recuperate menstruation. There are many varieties of peonies, the wild type and cultivars of purple dotted peony referred to herein as Xing-long-shan peony and primitive purple dotted peony varieties, respectively, have poor colors, humdrum appearance and fragrance, low yield of bark. Both decorative value and economic value are low. Shan-dong peony and He-nan peony also have poor colors, light fragrance and are susceptible to virus and pests. Moreover, they have some other disadvantages such as weak hardiness and drooping flowers.

Although hybridization between varieties of the peony for breeding new varieties having superior characters is well known in the art, however, selection of parental combinations having potential use in breeding is very difficult.

DISCLOSURE OF THE INVENTION

It is an object of the present invention to provide parental combinations useful in breeding purple dotted peonies.

The present inventor has investigated the main features and the distribution of Gan-su purple dotted peony (primitive purple dotted peony), and its status in domestic cultivation in China. Upon extensive investigation, he established the classification system of Chinese cultivated peonies, and concluded the regular pattern of feature inheritance from parent to filial generations, which is used as the guidance for carrying out cross breeding. He found that when the new purple dotted peony (F1) obtained through hybridization among the primitive purple dotted peony and between the wild type peony and the primitive purple dotted peony, which has black, brown and purple dots, thick fragrance, erect flowers with multi-colored petals, were hybridized with the Zhong-yuan peony, which has no dots, light fragrance, drooping flowers with pure and poor colors, a filial generation with more excellent characters were obtained, which has much varied dots, thick fragrance, erect flowers with rich and more varied colors. In other word, the superior characters of the new purple dotted peony is much enhanced in the filial generation of the hybridization of the new purple dotted peony and the Zhong-yuan peony. As the result of much research work within twenty years, 530 excellent peony varieties were obtained through parent selection, hybridization and screening. These new varieties include Bei-guo-feng-guang, Jin-cheng-wan-xia, Xing-long-shao-nv, Long-yuan-zhuang-shi, Bai-shang-hei-shui, Tian-shan-ri-chu, Yue-zhao-kun-lun, Qi-lian-cai-hong, Hong-xian-nv, He-ping-lan, Mai-ji-yan-yun, Lan-shan-jin-guang and He-ping-er-qiao, which have been widely planted in the areas of northeastern and northwestern part of China. They exhibit strong hardiness and great adaptability for various conditions.

Accordingly, the present invention provide a parental combination method for breeding purple dotted peonies, including firstly carrying out the hybridization among the primitive purple dotted peony and between the wild type peony and the primitive purple dotted peony, and then the resulting filial generation was hybridized with the Zhong-yuan peony.

The breeding of purple dotted peony in present invention is performed by means of single cross, reciprocal cross, three way cross and compound cross between carefully selected varieties and then directional selection in F1 or F2.

Specifically, said parental combinations include the following combinations:

1. Hybridization (single cross or reciprocal cross) among primitive purple dotted peonies such as Zhu-sha-hong, Qing-xin-bai, Da-ban-bai, Mei-gui-hong and Mei-ren-mian was carried out. Most of those primitive varieties have simple flowers, poor colors, short blooming period, tall plants, difficult for pot culture, too heavy fragrance, small leaves and high fruitification capacity that affects the blooming next year. By using parent selection, hybridization and screening, filial generations including Li-xiang, Hei-tian-e and Li-chun etc. with special variations and excellent features inherited from their parents were obtained (see example 1).

2. Hybridization (single cross or reciprocal cross) of the Xing-long-shan purple dotted peony (wild type) with primitive purple dotted peony such as Zhu-sha-hong, Meigui-hong, Da-xue-qing, Mei-ren-mian was carried out. The filial generations were improved in cold-resistance, drought-endurance, barren-endurance, pest-resistance and hardiness, with bright colored, erect flowers, and were more suitable for making bouquets. The obtained new varieties include Shu-sheng-peng-muo, Fen-he and Hong-lian etc.(see example 2).

3. Hybridization (three way cross or compound cross) of the Zhong-yuan peony (Shan-dong He-ze peony) with the new varieties of purple dotted peonies (F1) obtained in above 1 and 2, Xue-li-cang-jin, Jin-bo-dang-yang, Shi-he-lian and Zi-gong-du-xiu, was carried out. The filial generation inherited the excellent characteristics from their parents and shown special variations. A great number of rare varieties were obtained. Both of the excellent characteristics of Shan-dong He-ze peonies such as bright and pure colors, short plants, suitable for pot cultivation, and that of the purple dotted peonies such as grand plants, rich colors, thick fragrance, strong hardiness and erect flowers, are kept and improved in those filial generations. New varieties obtained in this regard include Qin-jin-zhi-hao, Qi-lian-cai-hong, Guang-mang-si-she and Xiu-lou-dian-cui etc. (see example 3).

Seeds of the following peony varieties have been deposited with the China General Microbiological Culture Collection Center (CGMCC) at P.O.Box 2714, Beijing 100080, P. R. China on Oct. 20, 1999 with their CGMCC numbers in parenthesis: 'Guo-hong' (CGMCC NO. 0425.1); 'Hong-lian' (CGMCC NO. 0425.2); 'Zhu-sha-hong' (CGMCC NO. 0425.3); 'Qing-xin-bai' (CGMCC NO. 0425.4); 'Da-ban-bai' (CGMCC NO. 0425.5); 'Mei-gui-hong' (CGMCC NO. 0425.6); 'Mei-ren-mian' (CGMCC NO. 0425.7); 'Xing-long-shan' (CGMCC NO. 0425.8); 'Da-xue-qing' (CGMCC NO. 0425.9); and 'Bei-guo-feng-guang' (CGMCC NO.0425.10).

EXAMPLES

The present invention will be described in detail with the following examples.

Example 1

Hybridization (single cross or reciprocal cross) among primitive varieties of purple dotted peonies such as Zhu-sha-hong, Qing-xin-ba, Da-ban-bai, Mei-gui-hong and Mei-ren-mian was carried out.

1) Qing-xin-ba×Da-ban-bai, the selected F1 was named Beiguo-feng-guang. It has big flowers with plural petal.
2) Zhu-sha-hong×Mei-gui-hong, the selected F1 was named Li-xiang. It has plural petal flowers with bright colors.
3) Zhu-sha-hong×Zhu-sha-hong, the selected F1 was named Hei-tiane. It's flowers has more melanin.
4) Mei-gui-hong×Zhu-sha-hong, the selected F1 was named Li-chun. It has advanced blooming period.

Example 2

Hybridization (single cross or reciprocal cross) between Xing-long-shan purple dotted peony (wild type) and the primitive purple dotted peonies such as Zhu-sha-hong, Mei-gui-hong, Da-xue-qing and Mei-ren-mian was carried out.

1) Xing-long-shan peony×Da-ban-bai, the selected F1 was named Shu-sheng-peng-muo. It's flowers has bigger dots which penetrated to the dorsal side of the petal.
2) Xing-long-shan peony×Mei-gui-hong, the selected F1 was named Fen-he. It has colorful flowers.
3) Xing-long-shan peony×Zhu-sha-hong, the selected F1 was named Hong-lian. It has erect flowers with long branches, which is more suitable for making bouquets.

Example 3

Hybridization (three way cross or compound cross) between Zhong-yuan peony (Shan-dong He-ze peony) and the new varieties of purple dotted peonies obtained in Example 1 and 2 such as Xue-li-cang-jin, Jin-bo-dang-yang, Shi-he-lian and Zi-gong-du-xiu was carried out.

1) Zhao-fen×Xue-liiang-jin, the selected F1 was named Qin-jin-zhi-hao. It has thick branches and big dot flowers with brown and black color, and pleasant smell.
2) Guo-hong×Jin-bo-dang-yang, the selected F1 was named Qi-lian-cai-hong. It has big flowers with brownish red dots.
3) Hong-lian×Shi-he-lian, the selected F1 was named Guang-mang-si-she. It's flowers has red ovary coat, red stigma and triangular purple dots.
4) Shan-dong No. 18×Zi-gong-du-xiu, the selected F1 was named Xiu-lou-dian-cui. It has step-shape flowers with pink color and blue-pink dots.

The present invention was made at the Peace Peony Garden in Yu-zhong town in Gan-su province. The climate conditions are: annual rainfall 348 mm, effective accumulation temperature 2500, absolute highest temperature 34.6° C., absolute lowest temperature −24.7° C., frost-free period 184 days, annual evaporative value 1700 mm. The soil is highland loess, 40–150 meters thick, serosem, pH 8.1. The attitude is 1750–1910 meters. Cultivation conditions are: irrigating 2–3 times annually, weeding and loosening the soil 34 times annually, fertilizer application one time, trimming 2 times (once in winter and once in summer). Germination takes place between March 24 and 30. The blooming period is from May 12 to 30. Maturation of the seed takes place from August 15 to September 1. Abscission of the leave takes place from October 15 to 25.

Screening of filial generations

Emasculation was carried out at a time between May 10 and 24, and pollination was carried out between May 15 and 27. The seed was harvested and sowed between August 8 and 30. Germination take place between March 25 and April 15 in the third spring after sowing. The first blooming take place between the fourth and the sixth year after germination. After blooming for three successive years, when the characters of the plant is stable, screening of the filial generation was carried out, including preliminary selection, re-selection, final selection and planting in the field.

The comparison between the new purple dotted peony varieties and the primitive varieties is shown in table 1–3.

TABLE 1

Comparison between primitive and filial generations

| ITEM | VARIETIES | |
|---|---|---|
| | PRIMITIVE PURPLE DOTTED PEONY VARIETIES | NEW PURPLE DOTTED PEONY VARIETIES F1 (BEI-GUO-FENG-GUANG) |
| Plant appearance | Tall | 80% tall, 20% medium and short |
| Branches | 95% long and slender, 5% thick and short | 20% thick and short |
| Leaves | 15 folioles, thin and small | 15 folioles, 20% of them grows to medium and big |
| Buds | Long and round, or small and round | 15% of them are big and round |
| Flowers | Erect | 95% of them are erect, 5% of them are drooping |
| Color | Rich colors, and most of them are compound colors | More rich and varied |
| Dots | Black, brown and purple dots | 10% red dots |
| Fragrance | Thick | Thick |
| Androecium | Yellow and white, slim or few filaments | 8% brownish red, no filaments or petalized |
| Pistil | 5 carpels, yellow and white, a few of them are red | More than 6 carpels, 15% red |
| Seed | small, high fructification capacity | 21% no seed |
| Blooming period | 18 days | 23 days |

TABLE 2

Comparison between parents and filial generations

| ITEM | VARIETY | |
|---|---|---|
| | XING-LONG-SHAN PEONY (WILD TYPE) | NEW PURPLE DOTTED PEONY VARIETIES F1 |
| Plant Appearance | Tall | Tall |
| Branch | Long and slender | Long and thick |
| Leaves | 15 folioles, thin and small | 5 folioles, 25% bigger than the wild type |
| Buds | Small and thin | Big and round |
| Flowers | Single petal, small, 11 × 5 CM | Plural petal, big, 16 × 8 CM |
| Color | Firstly pink then becomes white | White, pink, red, purple, blue and lilac |
| Dots | Small and black dots | Big and black, purple, red, brown dots |
| Fragrance | Thick | Thicker or medium |
| Androecium | Short filaments, Normal anthers | Long filaments, great change in anthers |
| Pistil | 5 carpels, white ovary coat and stigma | 5 carpels, some of them are red ovary coat and stigma |

TABLE 2-continued

Comparison between parents and filial generations

| ITEM | VARIETY | |
|---|---|---|
| | XING-LONG-SHAN PEONY (WILD TYPE) | NEW PURPLE DOTTED PEONY VARIETIES F1 |
| Seed | Small, large number | Big, decreased number |
| Blooming period | 15 days | 18 days |

TABLE 3

Comparison between parents and filial generations

| ITEM | VARIETY | | |
|---|---|---|---|
| | NEW PURPLE DOTTED PEONIES (F1) | ZHONG-YUAN PEONY | FILIAL GENERATIONS F1, F2 |
| Plant Appearance | Tall | Short | 80% tall, 12% medium and 8% small |
| Branch Leaves | Long and slender Hairy leave, 15 folioles, thin and small | Thick and short No hairy leave, 9 folioles, big and round | Long and thick 80% hairy leave, 85% 15 folioles, 15% 9 folioles, big and round |
| Buds | Long and round, or small and round | Big and round, | big and round |
| Flowers | Erect | Drooping, covered by leaves | erect, varied shape |
| Color | Multi-colored petals, and beautiful colors | Pure and poor | Rich and more varied |
| Dot color | Black, brown and purple dots | No dots | The pattern of the dots is much varied. Many patterns of red dots appeared. |
| Fragrance | Thick | Light | Thick |
| Androecium | Yellow and white, Slim filaments | Red and short filaments | The shapes and colors is much varied |
| Pistil | 5 carpels, yellow and white | 5 carpels, brownish red ovary coat and stigma | 0 to 13 carpel. The shape and color is much varied. |
| Seed | High genetic conservatism, high fructification capacity, small seeds | Much genetic mutation and atavism occured, low fructification capacity | No or high fructification capacity. Big seeds |
| Blooming period | 23 days | 25 days | 28 days |

What is claimed is:

1. A breeding method of purple dotted peonies, wherein, the hybridization among the primitive purple dotted peonies or between the wild type peonies and the primitive purple dotted peonies was firstly carried out, and then the resulting filial generation was hybridized with 'Guo-hong' (CGMCC NO. 0425.1) or 'Hong-lian' (CGMCC NO. 0425.2), wherein, said hybridization among the primitive purple dotted peonies or between the wild type peonies and the primitive purple dotted peonies is the hybridization with one of the following parental combinations:

(1) hybridization among primitive purple dotted peony varieties such as 'Zhu-sha-hong' (CGMCC NO. 0425.3), 'Qing-xin-bai' (CGMCC NO. 0425.4), 'Da-ban-bai' (CGMCC NO. 0425.5), 'Mei-gui-hong' (CGMCC NO. 0425.6) and 'Mei-ren-mian' (CGMCC NO.0425.7);

(2) hybridization between the 'Xing-long-shan' CGMCC NO. 0425.8) purple dotted peony (wild type) and the primitive purple dotted peony varieties such as 'Zhu-sha-hong' (CCGMCC NO.0425.3), 'Mei-gui-hong' (CGMCC NO.0425.6), 'Da-xue-qing' (CGMCC NO.0425.9) and 'Mei-ren-mian' (CGMCC NO. 0425.7).

2. The breeding method according to claim 1, wherein, the hybridization among primitive purple dotted peony varieties such as 'Zhu-sha-hong' (CGMCC NO. 0425.3), 'Qing-xin-bai' (CGMCC NO. 0425.4), 'Da-ban-bai' (CGMCC NO. 0425.5), 'Mei-gui-hong' (CGMCC NO. 0425.6) is the hybridization with the combination of 'Qing-xin-bai' (CGMCC NO. 0425.4)×'Da-ban-bai' (CGMCC NO. 0425.5), the selected F1 designated 'Bei-guo-feng-guang' (CGMCC NO. 0425.10).

3. A peony variety designated 'Bei-guo-feng-guang' (CGMCC NO. 0425.10).

\* \* \* \* \*